(12) United States Patent
Dukhan

(10) Patent No.: US 8,932,059 B2
(45) Date of Patent: Jan. 13, 2015

(54) DENTAL IMPLANT AND METHOD OF IMPLANTATION

(71) Applicant: Mazen Dukhan, Edelb (SY)

(72) Inventor: Mazen Dukhan, Edelb (SY)

( * ) Notice: Subject to any disclaimer, the term of this patent is extended or adjusted under 35 U.S.C. 154(b) by 0 days.

(21) Appl. No.: 14/151,322

(22) Filed: Jan. 9, 2014

(65) Prior Publication Data

US 2014/0141388 A1    May 22, 2014

Related U.S. Application Data

(63) Continuation-in-part of application No. 13/568,283, filed on Aug. 7, 2012, now abandoned.

(51) Int. Cl.
*A61C 8/00*    (2006.01)

(52) U.S. Cl.
CPC ............. *A61C 8/0025* (2013.01); *A61C 8/0068* (2013.01); *A61C 8/008* (2013.01); *A61C 8/006* (2013.01); *A61C 8/0089* (2013.01); *A61C 8/0059* (2013.01); *A61C 8/0063* (2013.01)
USPC ........................................ 433/174; 433/201.1

(58) Field of Classification Search
CPC .................................................... A61C 8/0022
USPC ........................................ 433/173–175, 201.1
See application file for complete search history.

(56) References Cited

U.S. PATENT DOCUMENTS

| | | | |
|---|---|---|---|
| 1,698,951 A * | 1/1929 | Holmes ......................... | 411/453 |
| 3,207,023 A * | 9/1965 | Knohl ......................... | 411/387.3 |
| 5,087,201 A * | 2/1992 | Mondani et al. .............. | 433/174 |
| RE34,969 E * | 6/1995 | Dixon et al. .................. | 411/412 |
| 5,743,914 A * | 4/1998 | Skiba ............................ | 606/304 |
| 5,967,783 A * | 10/1999 | Ura ............................... | 433/174 |
| 6,135,772 A * | 10/2000 | Jones ............................ | 433/174 |
| 6,234,797 B1 * | 5/2001 | Ura ............................... | 433/174 |
| 6,273,722 B1 * | 8/2001 | Phillips ........................ | 433/174 |
| 6,743,233 B1 * | 6/2004 | Baldwin et al. .............. | 606/323 |
| 6,746,244 B2 * | 6/2004 | Riley et al. ................... | 433/173 |
| D565,181 S * | 3/2008 | Anitua Aldecoa ........... | D24/156 |
| D588,700 S * | 3/2009 | Anitua Aldecoa ........... | D24/156 |
| 7,806,693 B2 * | 10/2010 | Hurson ......................... | 433/174 |
| D689,610 S * | 9/2013 | Dukhan ........................ | D24/156 |
| 8,758,012 B2 * | 6/2014 | Hurson ......................... | 433/173 |
| 2007/0099153 A1 * | 5/2007 | Fromovich .................... | 433/174 |
| 2008/0261175 A1 * | 10/2008 | Hurson ......................... | 433/173 |
| 2010/0304335 A1 * | 12/2010 | Garcia Saban et al. ....... | 433/174 |
| 2011/0033826 A1 * | 2/2011 | Chen ............................ | 433/174 |
| 2011/0294094 A1 * | 12/2011 | Moshavi ....................... | 433/174 |
| 2013/0224687 A1 * | 8/2013 | Karmon ....................... | 433/174 |
| 2014/0045144 A1 * | 2/2014 | Dukhan ........................ | 433/174 |

* cited by examiner

*Primary Examiner* — Cris L Rodriguez
*Assistant Examiner* — Hao D Mai
(74) *Attorney, Agent, or Firm* — Stuart M. Goldstein

(57) ABSTRACT

A self-tapping dental implant has a unitary body with an open end and a bottom tip end. The implant is tapered downward from the open top to the tip end and has an internal cavity extending for substantially the length of the implant. Smooth inner sidewalls are located at the upper end of the cavity and internal threads extend from the sidewalls down into the cavity. The dental implant method utilizes the unique dental implant, along with a flexible sleeve, a solid abatement member, and dental attachment screw, to place the implant with minimal patient trauma, while simulating the micro-movement of a natural tooth.

1 Claim, 17 Drawing Sheets

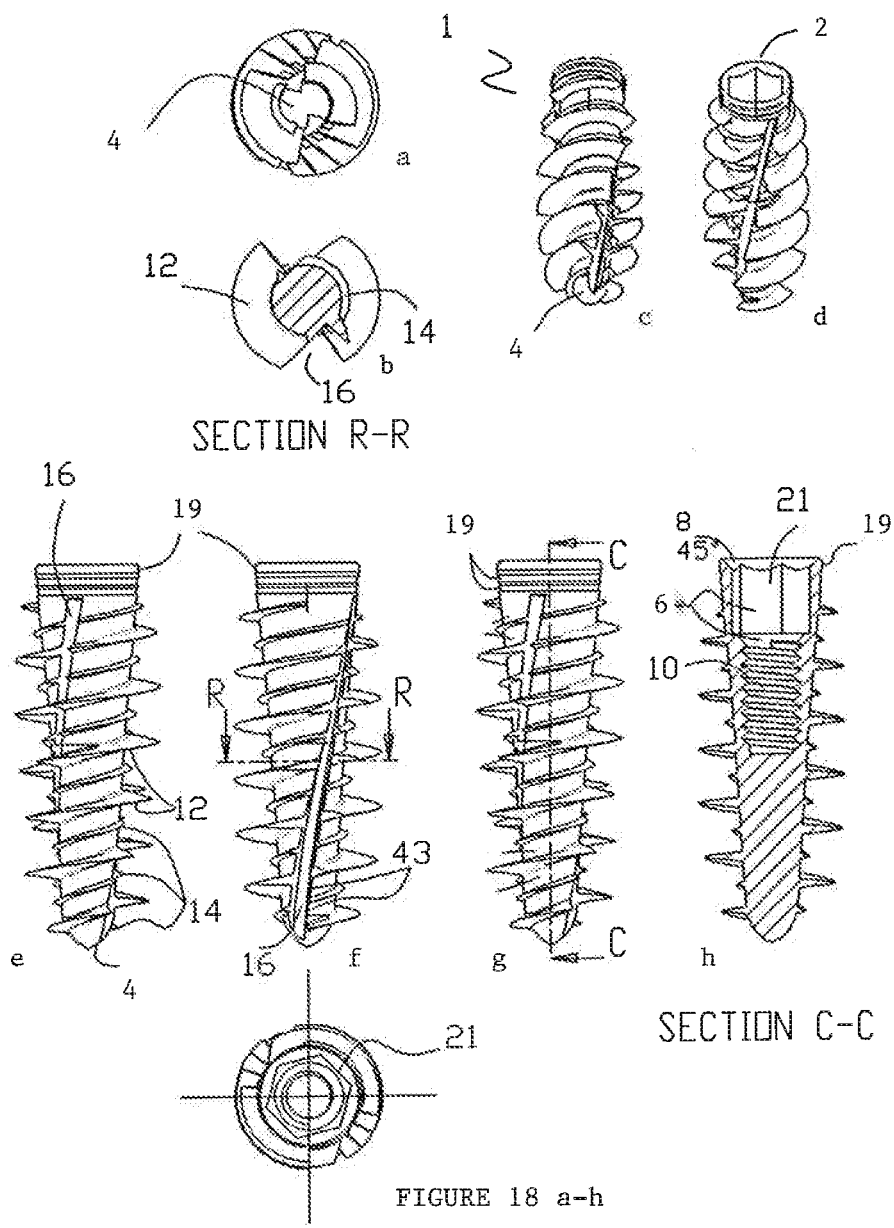
FIGURE 18 a-h

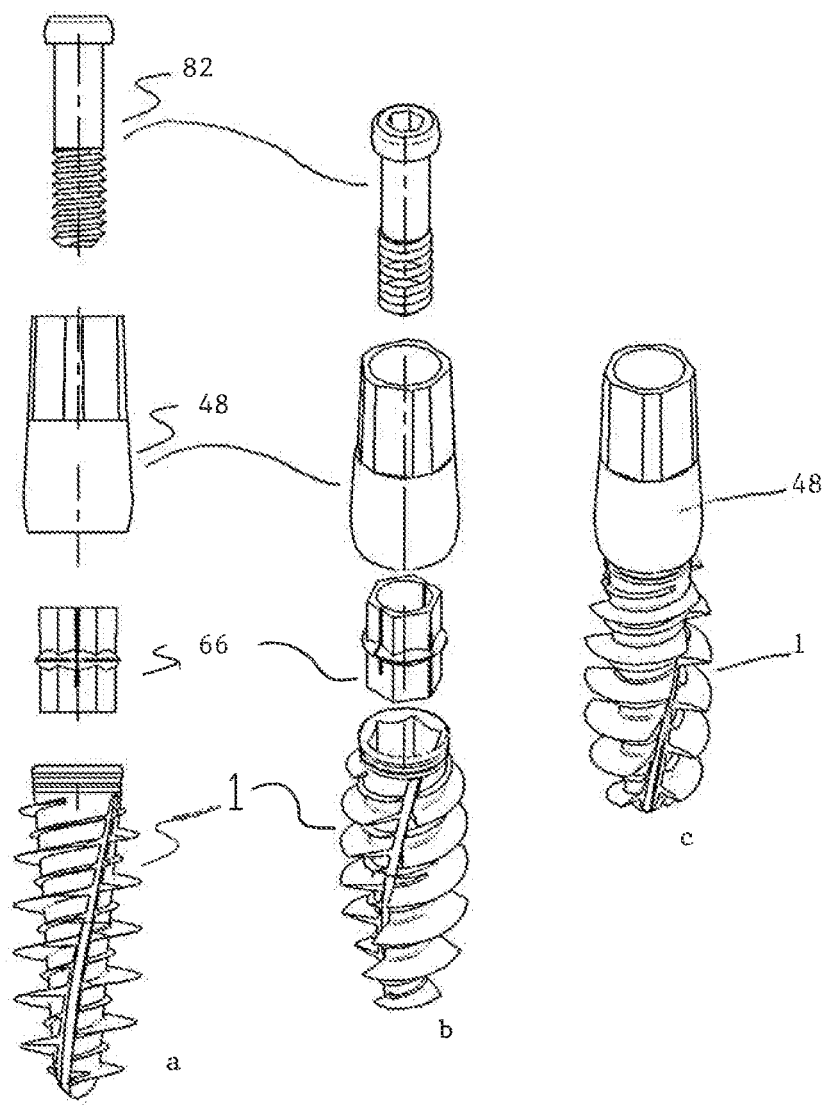
FIGURE 19 a-c

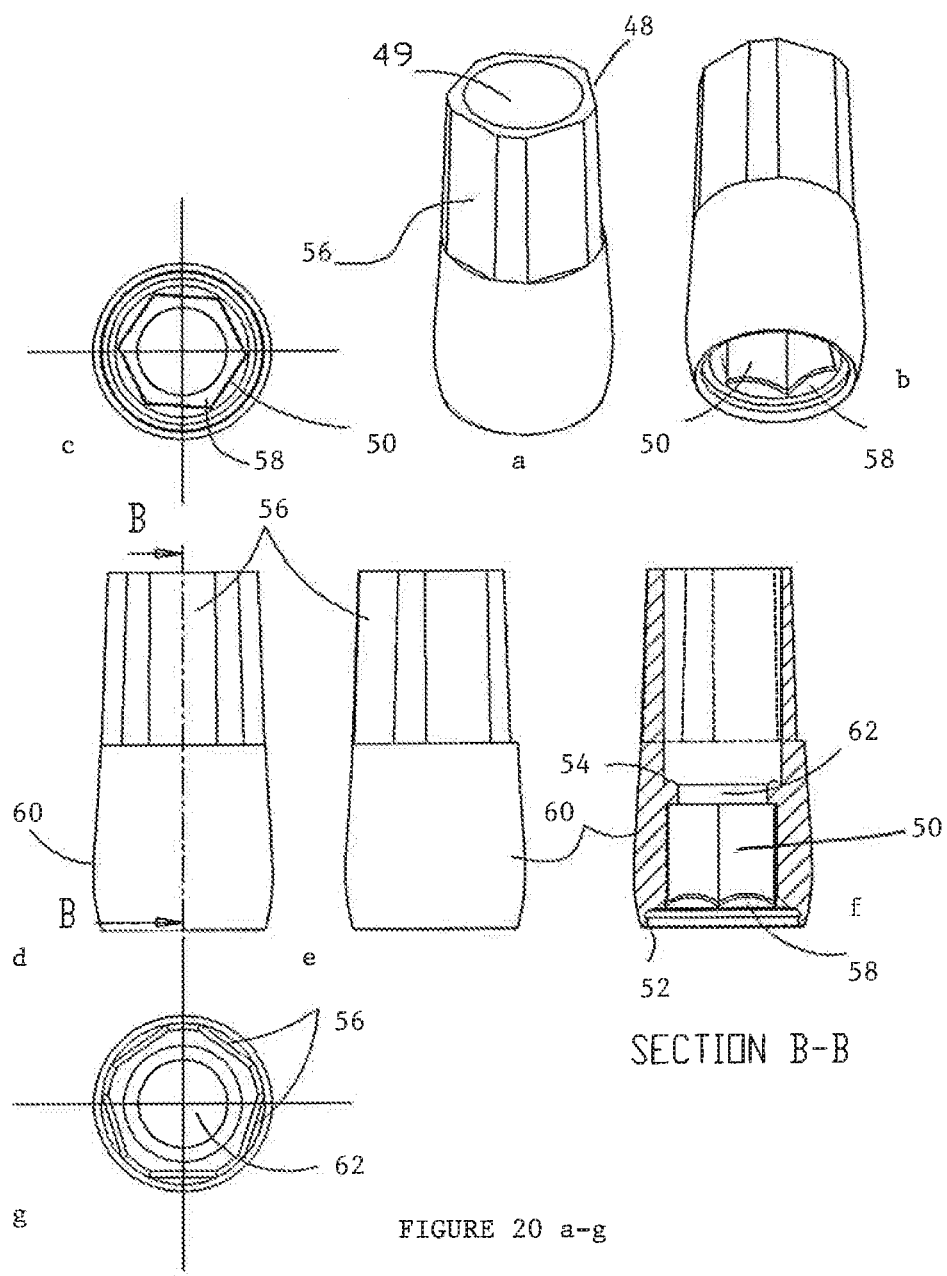
FIGURE 20 a-g

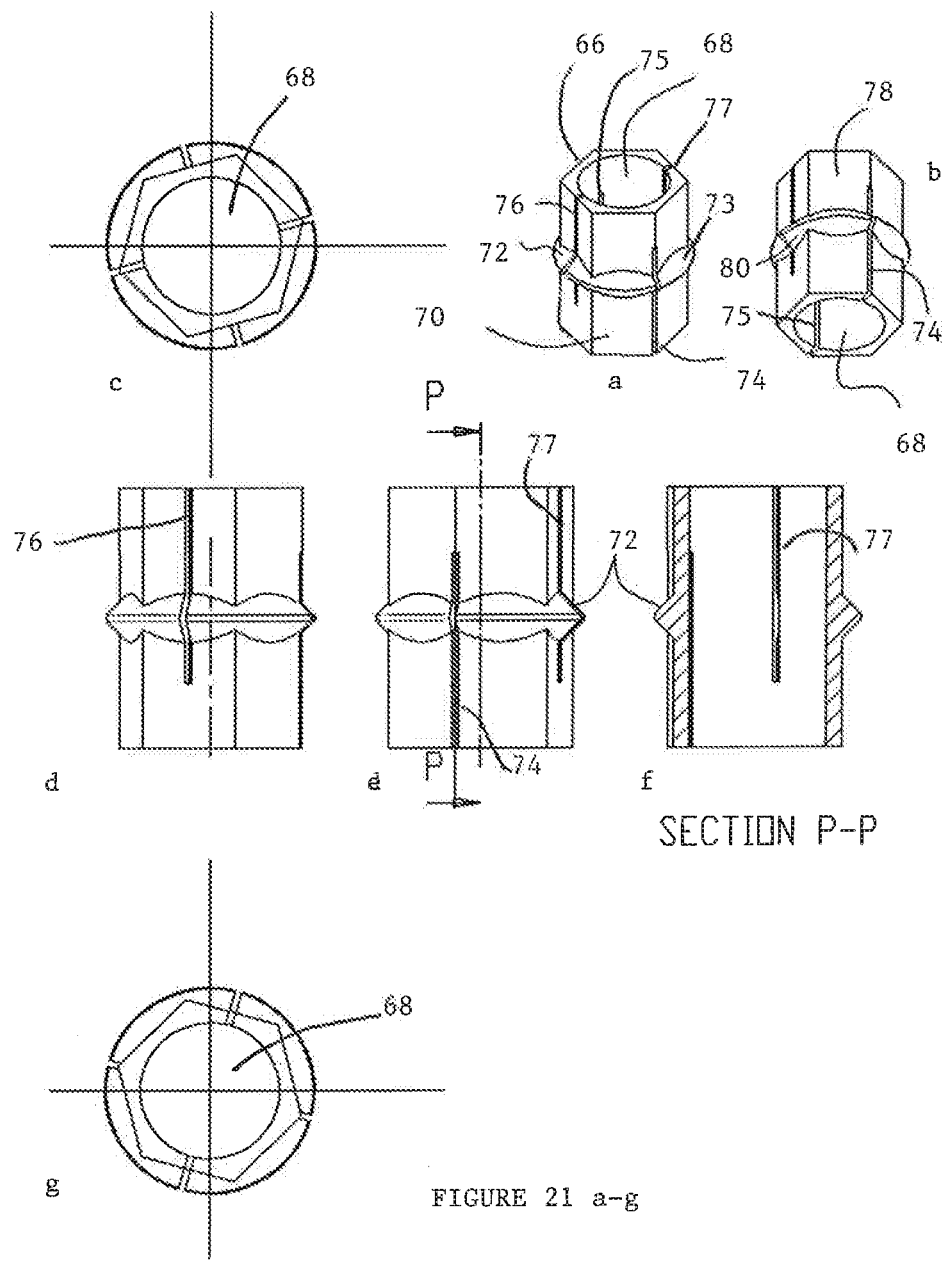
FIGURE 21 a-g

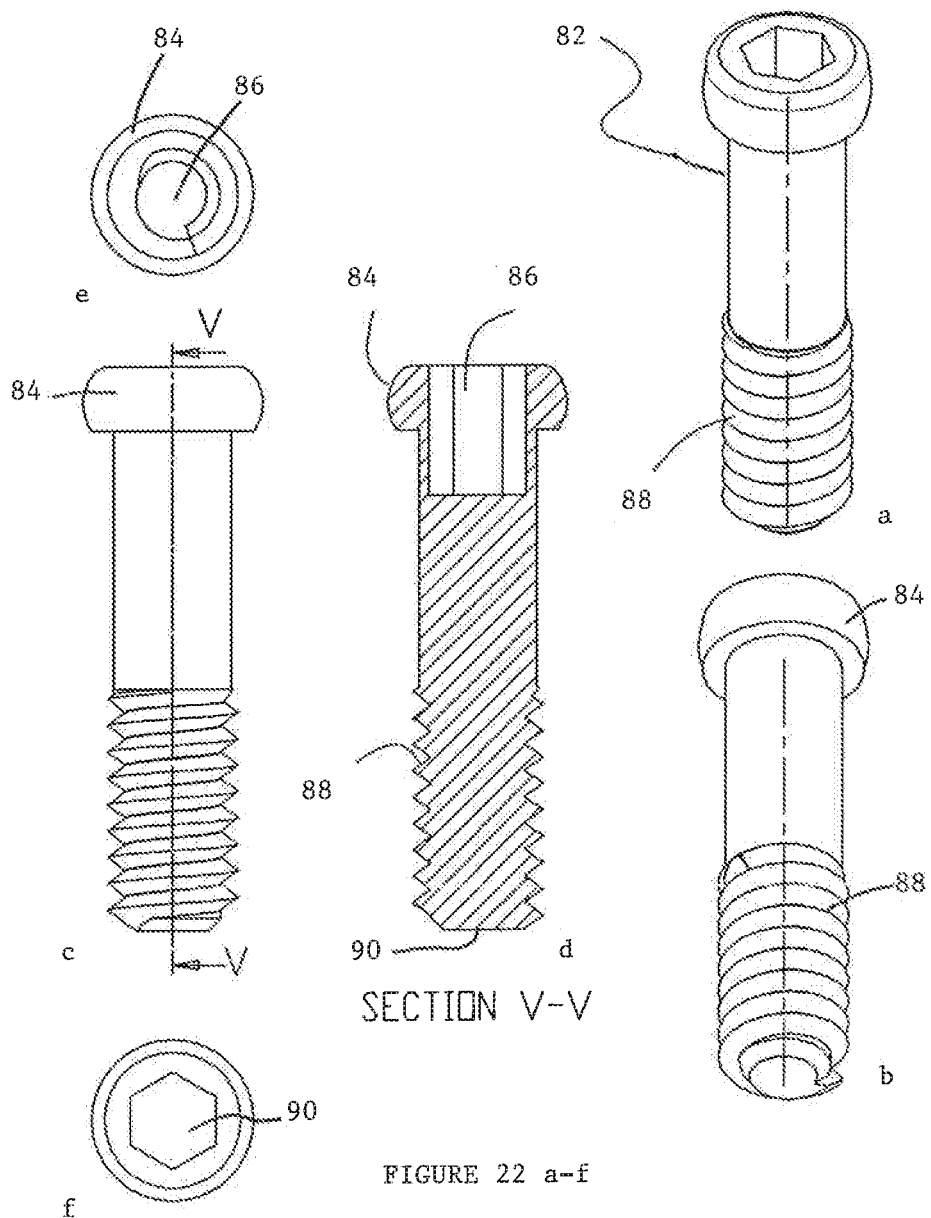
FIGURE 22 a-f

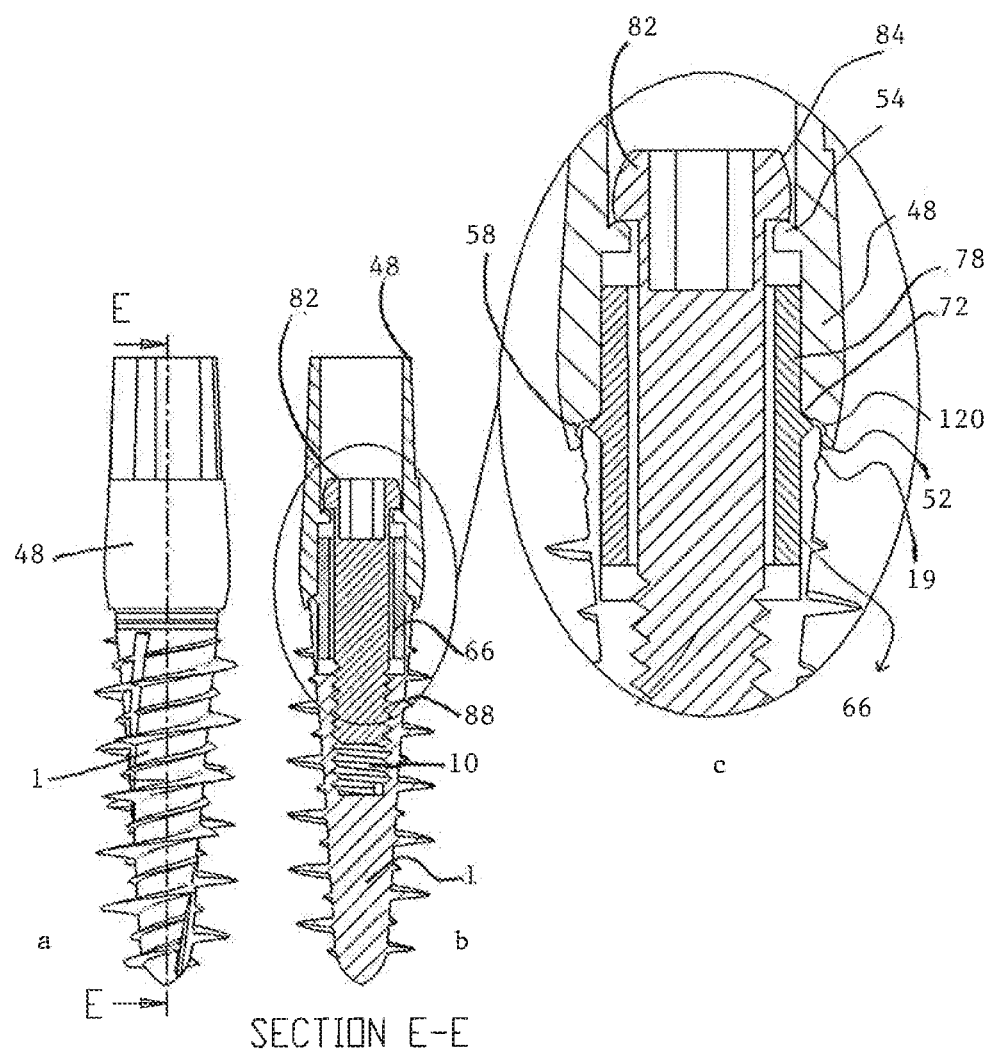
FIGURE 23 a-c

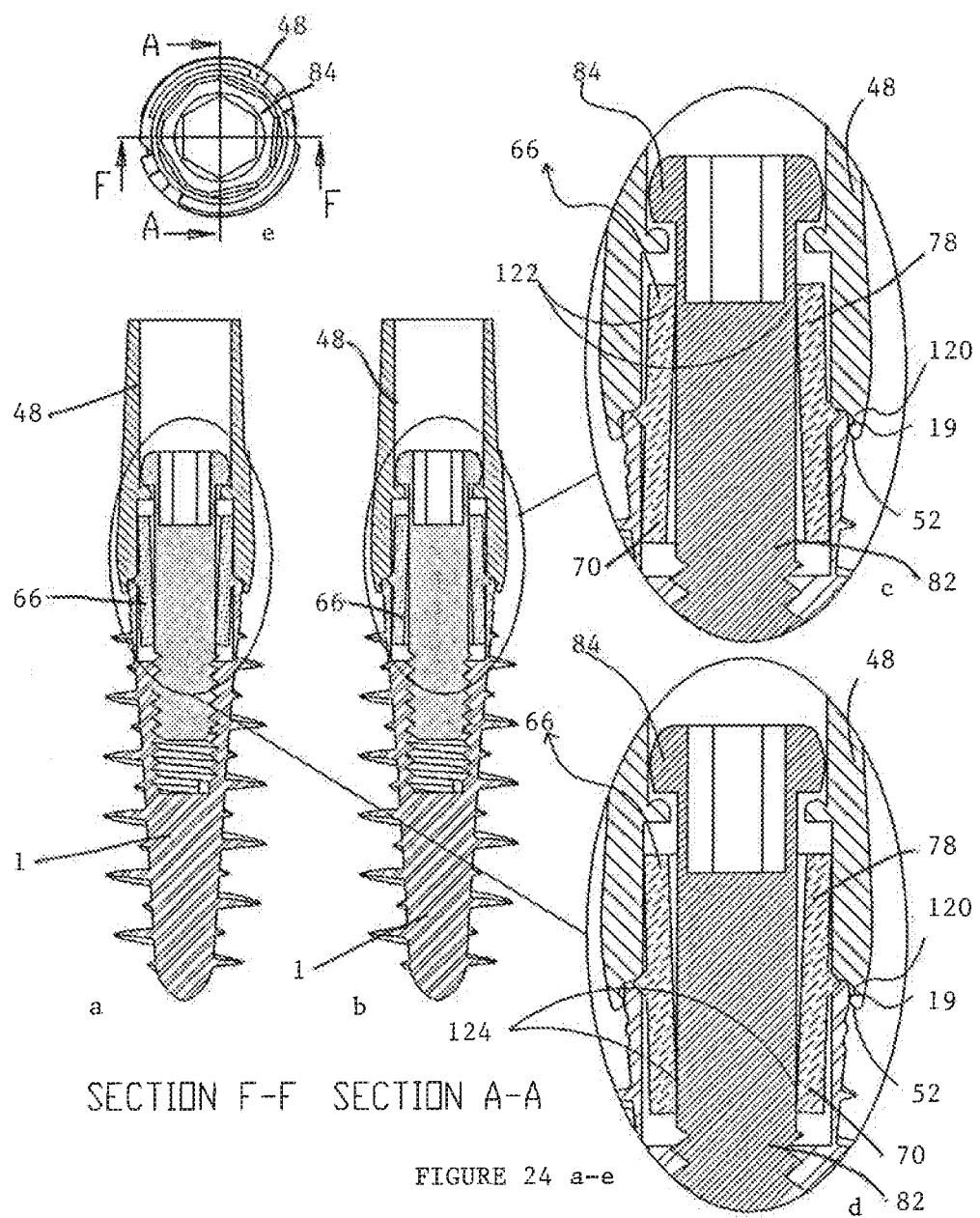
SECTION F-F  SECTION A-A
FIGURE 24 a-e

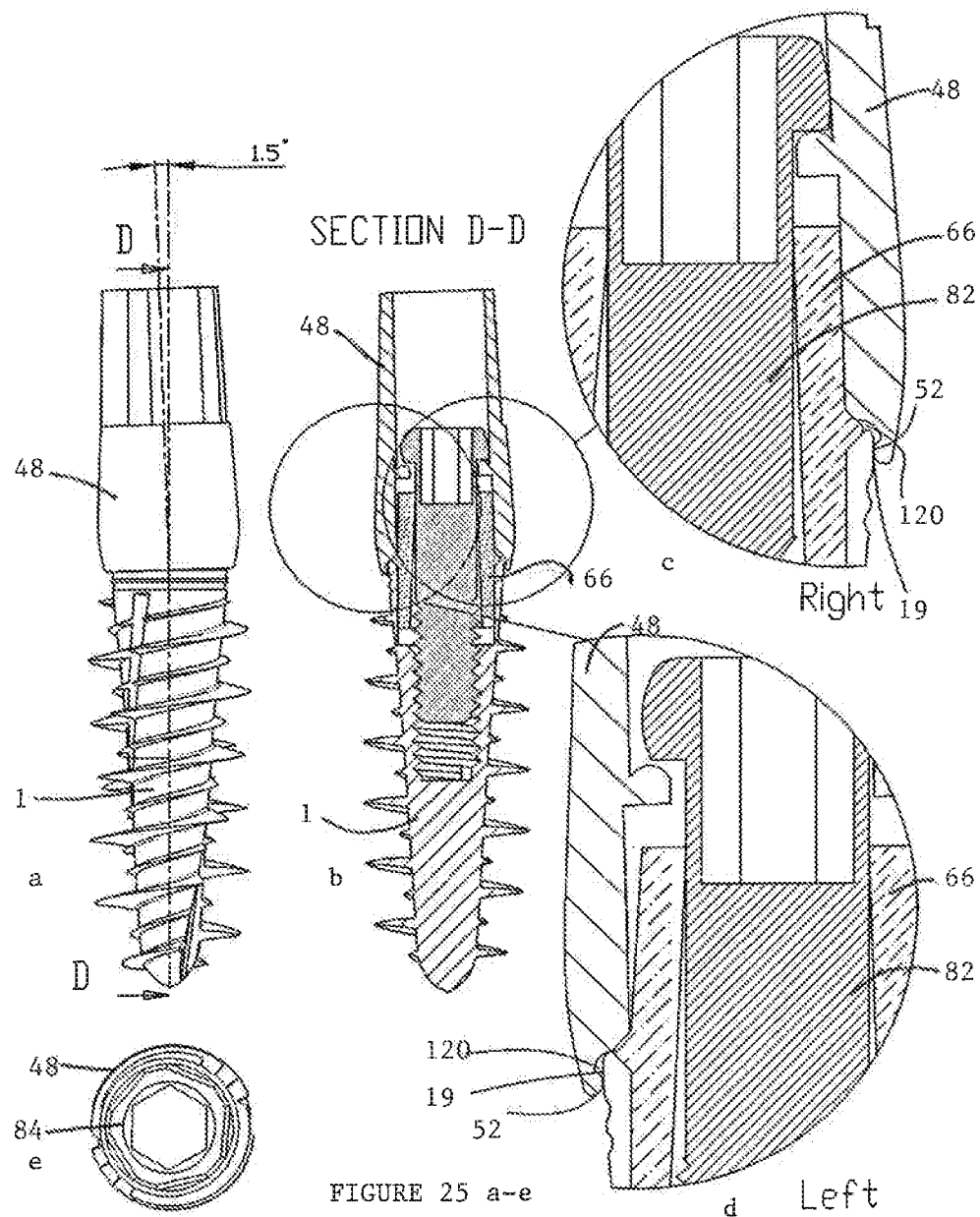
FIGURE 25 a-e

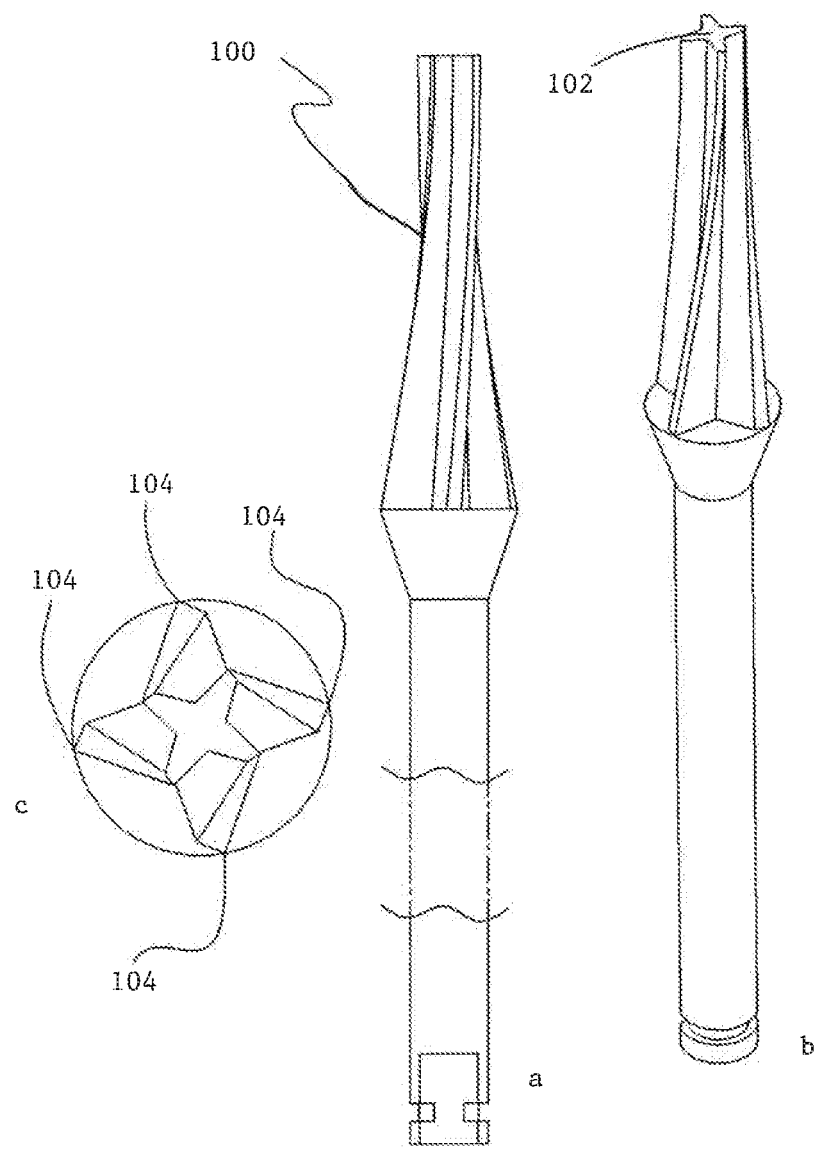
FIGURE 26 a-c

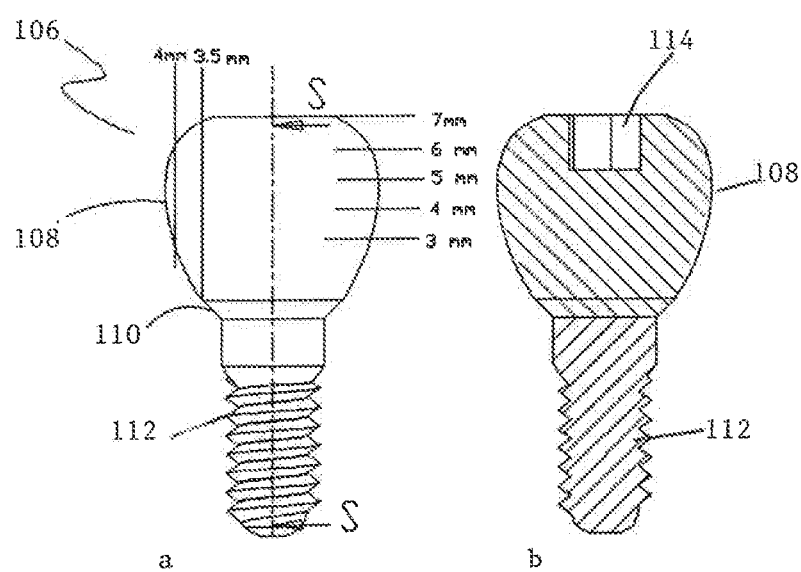
FIGURE 27 a-b

DENTAL IMPLANT AND METHOD OF IMPLANTATION

RELATED APPLICATION

The herein application is a continuation-in-part of non-provisional application Ser. No. 13/568,283, filed on Aug. 7, 2012.

FIELD OF THE INVENTION

The present invention relates to a dental implant and a method for surgically implantation of the dental implant with a flexible abutment member which simulates the flexibility of a natural tooth and which supports a prosthetic crown as a replacement for the tooth.

BACKGROUND OF THE INVENTION

Prosthetic dental devices are very often necessary to replace natural teeth which are lost due to infection, disease, or some type of trauma. The dental endosteal or endosseous implant utilized for this practice is surgically implanted within the patient's mandibular or maxillary alveolar bone. After the gum and bone from the implantation process has healed, the implant is fitted with a tooth-simulating prosthesis or crown.

However, current implants and their methods of implantation have a number of limitations and disadvantages. For instance, most dental implant procedures require the installation of implants which protrude out of the gum and are thus exposed. This results both in prolonged discomfort for the patient and the possibility of implant malformation or failure during the initial healing process. Protruding devices also subject the effected area to infection or gum disease. Current methods also employ dental implants which often are unstable or which do not efficiently and/or effectively tap into the bone, thus creating additional problems for patient and dentist. Moreover, the use of known dental implants and implant techniques require excessive dental hardware, resulting in a more time consuming process and greater expense. Significantly, the time period necessary to complete the dental implant implantation to finished crown procedure, including the allowance of an adequate healing period, is lengthy, usually at least six months.

In addition, while dental implants are commonly inserted into prepared jaw bone sites as a fixture for a dental crown, prosthetic dental bridge, or other dental appliance, known implants will not simulate the natural tooth, which is supported by its periodontal ligament, from occlusal forces. These three occlusal forces, apical-coronal, buccal-lingual, and mesial-distal, can press a tooth in a certain direction, thereby meeting resistance from the periodontal ligament. The stress generated around the tooth is distributed around and, in effect, cushions the tooth for maximum protection. There is thus little movement, termed micro-motion, of the tooth in its socket. However, there is no periodontal ligament around a dental implant, so the result is that there is no cushion protection.

Current implants and their installation methods utilize a surgical flap, a procedure which requires prolong discomfort for the patient and multiple sutures. Protruding devices also subject the effected area to infection or gum disease. Current methods also require many drilling sequences, with excessive dental hardware, in order to insert a given implant, depending on the implant's size and shape. Usually the drill is not much smaller than the size of the implant. For instance a 3.5 mm drill is suitable to fit a 3.6 mm or 3.7 mm dental implant. Clinically, in many cases, the width of bone is very small, e.g. 3-4 mm, so there are no additional size options for the suitable implant size which is needed, particularly when the patient is in discomfort, due to bone grafting and other procedures.

SUMMARY OF THE INVENTION

It is thus the object of the present invention to provide a dental implant and method of implantation which overcomes the disadvantages and limitations of prior implants and methods of their use.

It is an object of the present invention to provide a dental implant which is uniquely configured to be tapped into the bone of the patient efficiently and effectively with the least trauma to the patient during the procedure.

It is another object of the present invention to provide a dental implant which provides a high degree of initial implant stability during the implantation process.

It is a further object of the present invention to provide a dental implant which has a back tapered coronal design for maximum alveolar volume and improved soft tissue support.

It is still another object of the present invention to provide a dental implant which has an upper platform for greater soft tissue interface.

It is another object of the present invention to provide a dental implant which, in its method of implantation, is readily adaptable for use with a healing screw, a unique abatement member, and ultimately a permanent prosthesis or crown.

It is the object of the present invention to provide a method of implantation of the uniquely configured dental implant described herein which provides less drilling into the patient's bone and thus minimum trauma to the patient.

It is a further object of the present invention to provide a dental implantation method Which utilizes minimal dental hardware and thus reduces the period of time for the implantation process and the expense of the process.

It is still another object of the present invention to provide a dental implantation method which utilizes a flexible abutment which simulates the micro-movement of a natural tooth, serving as a cushion to provide protection from unexpected forces affecting the implant, reducing trauma and complications, reducing healing time, and providing an implant which can be connected to a natural tooth or dental prosthetic bridge or like dental appliance.

It is a further object of the present invention to provide a dental implant implantation method which materially reduces the healing time and ultimately the time before which a permanent crown or prosthesis can be secured.

These and other objects are accomplished by the present invention, a self-tapping dental implant which has a unitary body with an open end and a bottom tip end. The implant is tapered downward from the open top to the tip end and has an internal cavity extending for substantially the length of the implant. Smooth inner sidewalls are located at the upper end of the cavity and internal threads extend from the sidewalls down into the cavity. The dental implant method utilizes the unique dental implant, along with a flexible sleeve, a solid abatement member, and dental attachment screw, to place the implant with minimal patient trauma, while simulating the micro-movement of a natural tooth.

The novel features which are considered as characteristic of the invention are set forth in particular in the appended claims. The invention, itself, however, both as to its design, construction and use, together with additional features and advantages thereof, are best understood upon review of the following detailed description with reference to the accompanying drawings.

BRIEF DESCRIPTION OF THE DRAWINGS

FIGS. 18a-h show various additional views of the dental implant of the present invention.

FIGS. 19a-c show the dental components utilized in the alternate dental implantation method of the present invention.

FIGS. 20a-g show various views of the abatement member used in the alternate dental implantation method of the present invention.

FIGS. 21a-g show various views of the flexible sleeve utilized in the alternate dental implantation method of the present invention.

FIGS. 22a-f show various views of the dental screw utilized in the alternate dental implantation method of the present invention.

FIGS. 23a-c show the various components of the alternate dental implantation method of the present invention joined as they would be positioned to receive a crown, dental bridge, or other dental prosthesis.

FIGS. 24a-e illustrate the effect of vertical, micro-movement of the dental implant in accordance with the alternate dental implantation method of the present invention.

FIGS. 25a-e illustrate the effect of lateral micro-movement of the dental implant in accordance with the alternate dental implantation method of the present invention.

FIGS. 26a-c show various views of the drill utilized in the alternate dental implantation method of the present invention.

FIGS. 27a-b show views of the healing screw utilized in the alternate dental implantation method of the present invention.

DETAILED DESCRIPTION OF THE INVENTION

Figure 1:
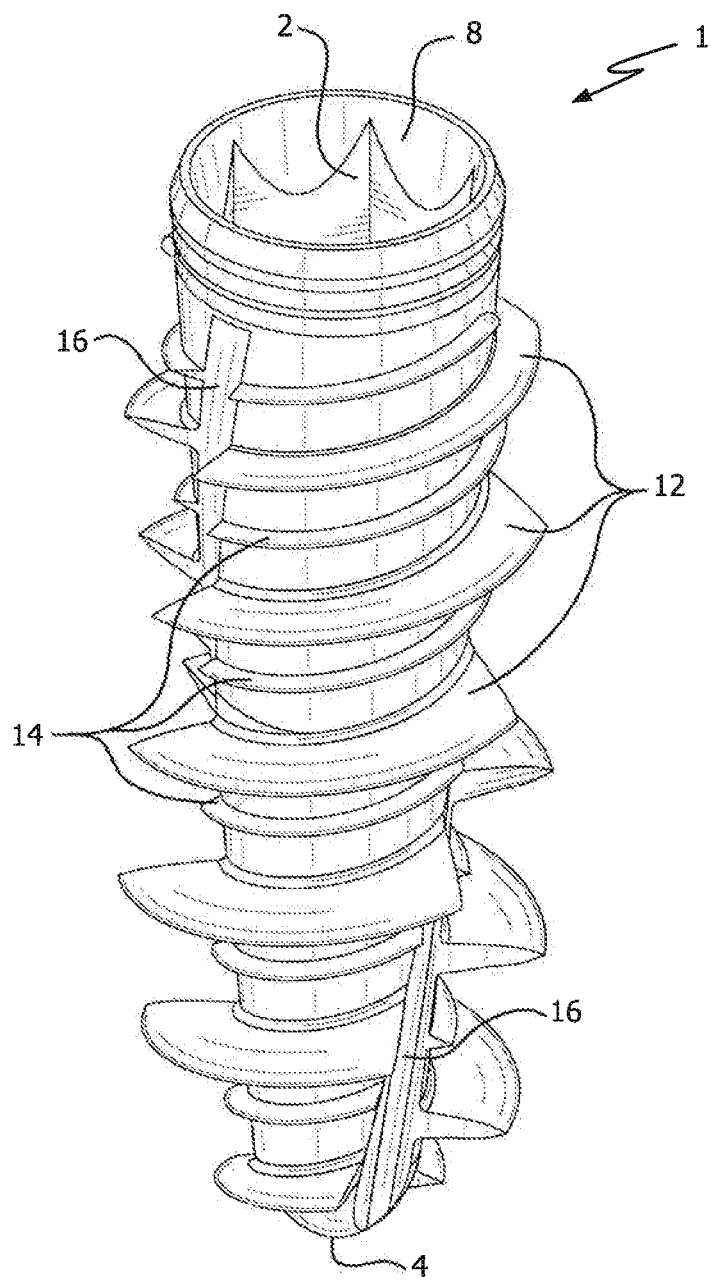
FIG. 1 is a perspective view of the dental implant of the present invention.
Figures 2, 3:
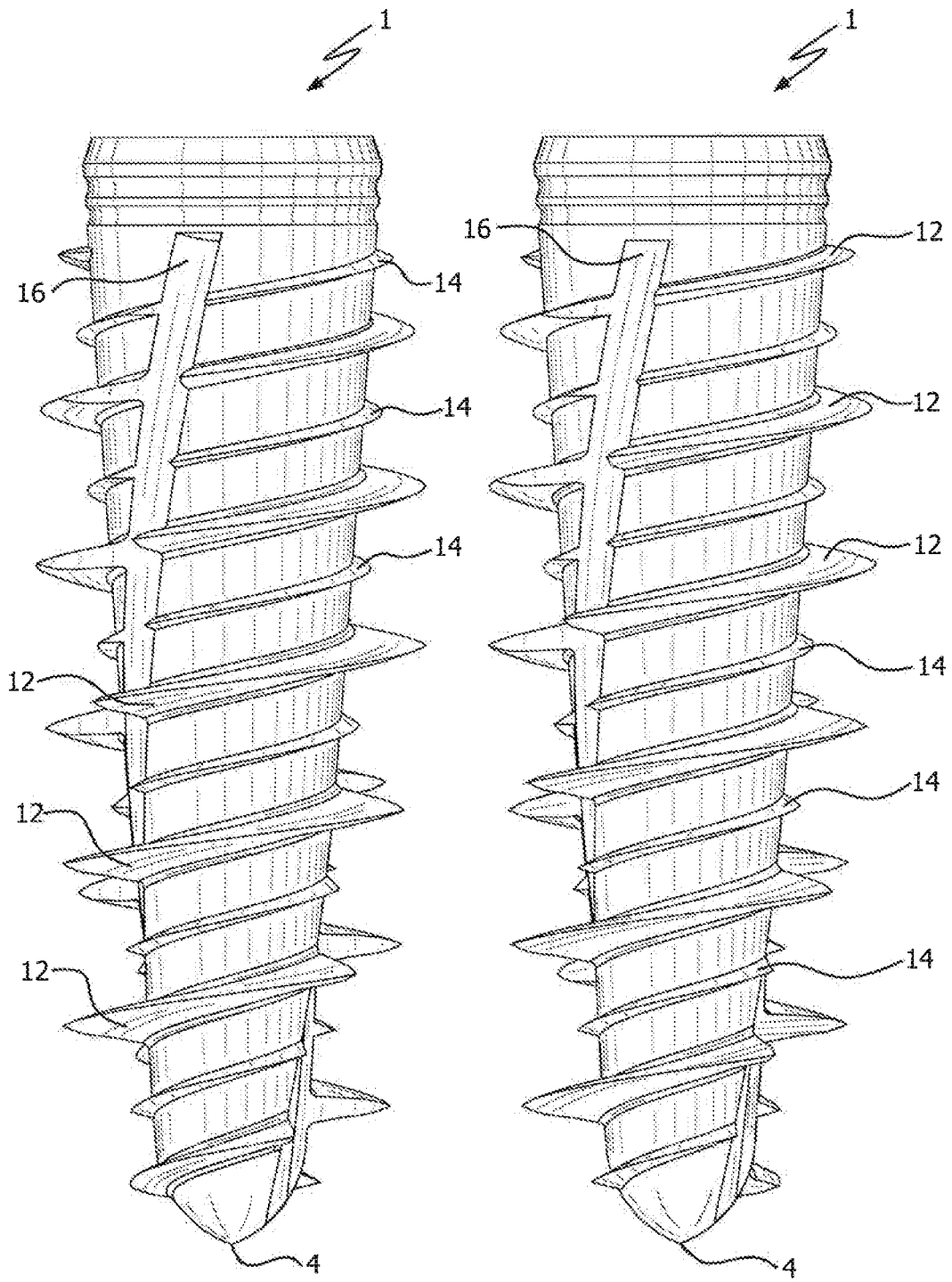
FIG. 2 is an elevation view of the dental implant of the present invention.
FIG. 3 is another elevation view of the dental implant of the present invention.
Figures 4, 5:
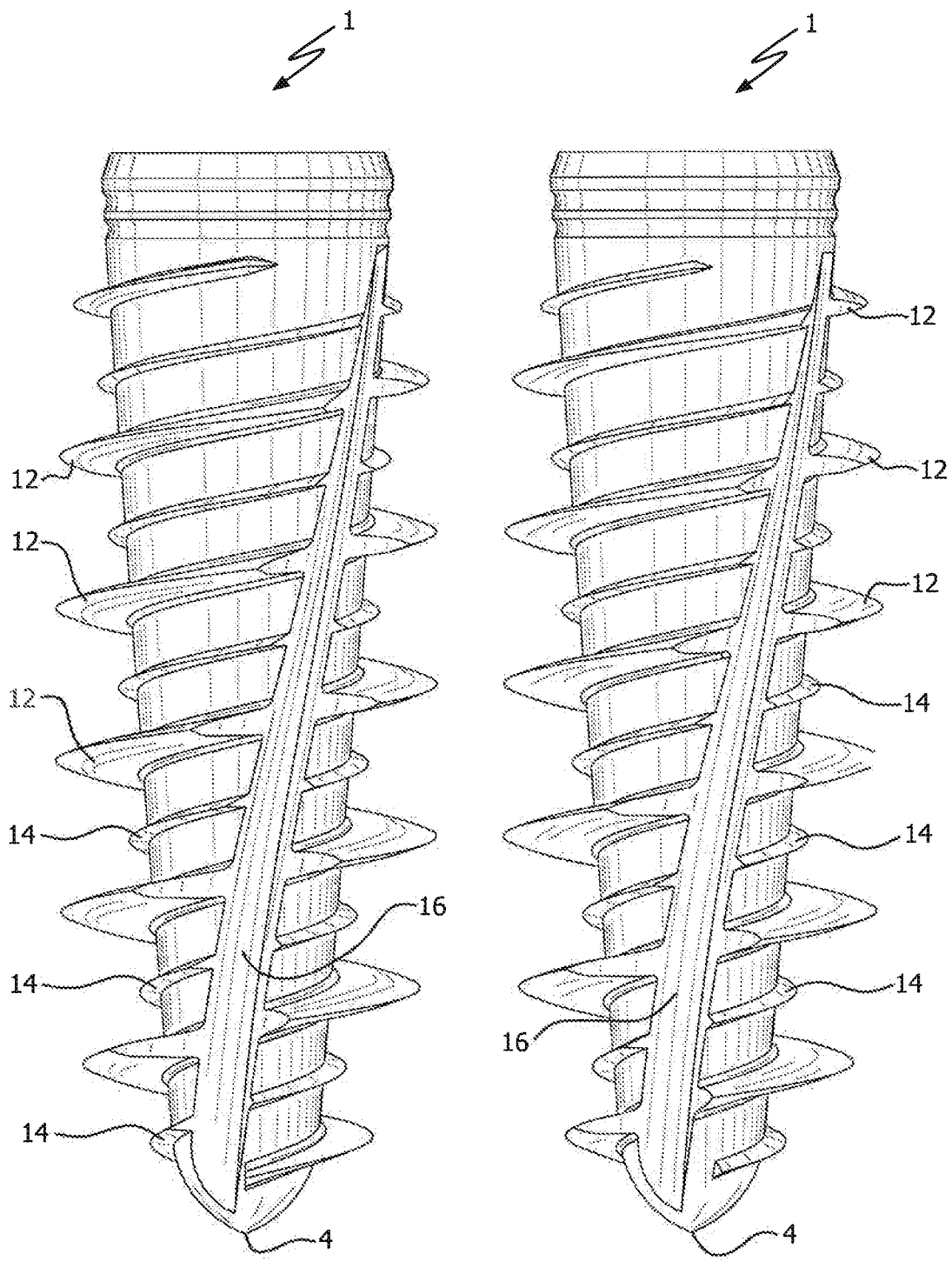
FIG. 4 is still another elevation view of the dental implant of the present invention.
FIG. 5 is another elevation view of the dental implant of the present invention.
Figure 6:
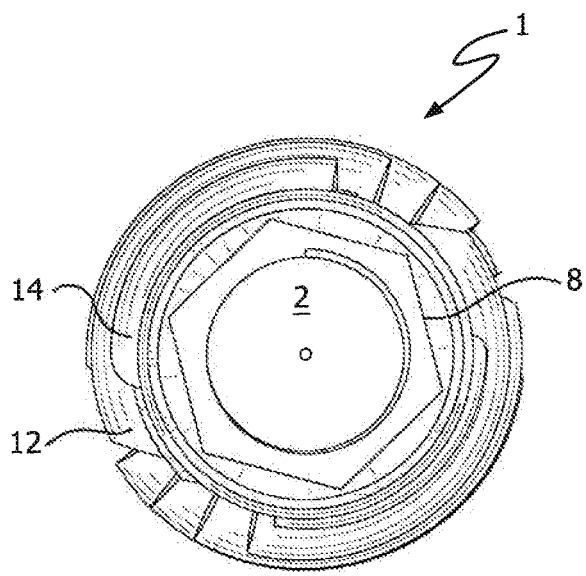
FIG. 6 is a top view of the dental implant of the present invention.
Figure 7:
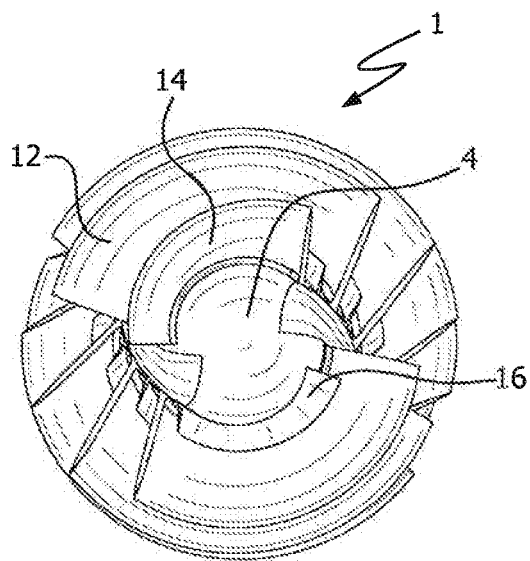
FIG. 7 is a bottom view of the dental implant of the present invention.
Figure 8:
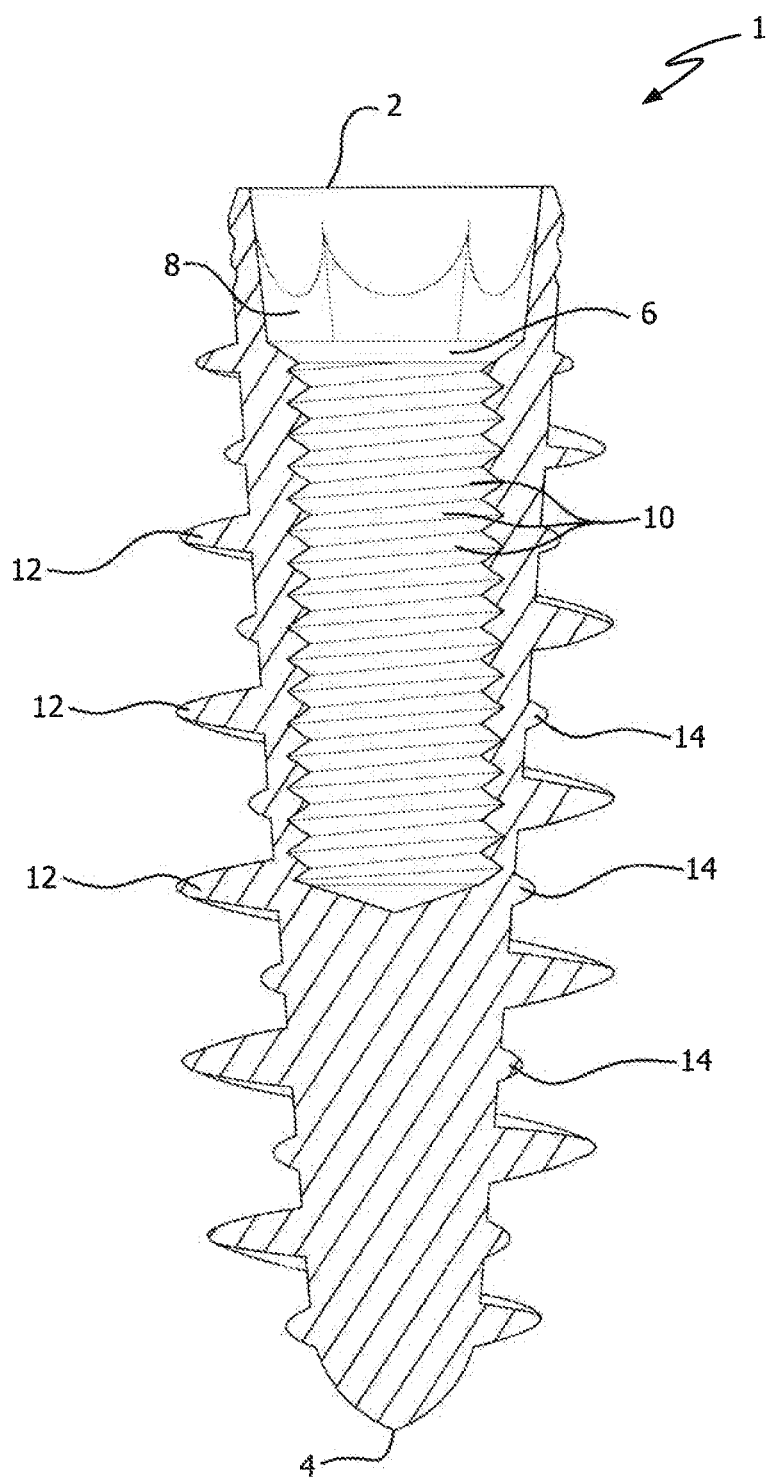
FIG. 8 is a cross-sectional view of the dental implant of the present invention.

As seen in FIGS. 1-8 and 18 self-tapping dental implant 1 is a unitary body having open top 2 and bottom tip end 4. Dental implant 1 is tapered downward from open top 2 to tip end 4. Internal cavity 6 extends from open top 2 down into dental implant 1. Smooth inner conical sidewalls 8 are located at the upper end of cavity 6. Hexagonal side walls 21 extend down cavity 6 to internal threads 10, which extend from the sidewalls down into the cavity. Smooth, cylindrical external side walls 19 extend around the top of implant 1. These side walls are polished and appear as a shiny ring tapered from and surrounding top 2.

Helical, wide pitch threads 12, having sharp, bladed edges extend along the exterior surface of implant 1. Smaller, helical, micro-threads 14, also with sharp blade edges, extend along the exterior surface and are located between the helical threads 12. Channel 16 with sharp bone cutting edge blade 43 encircles and spirals around the entire outside surface of implant 1. The channel extends through all of the helical threads 12 and 14, running obliquely, at an angle, from a location just below open top 2 to a location just above bottom tip end 4, 360° around implant 1.

Figures 9, 10, 11, 12:
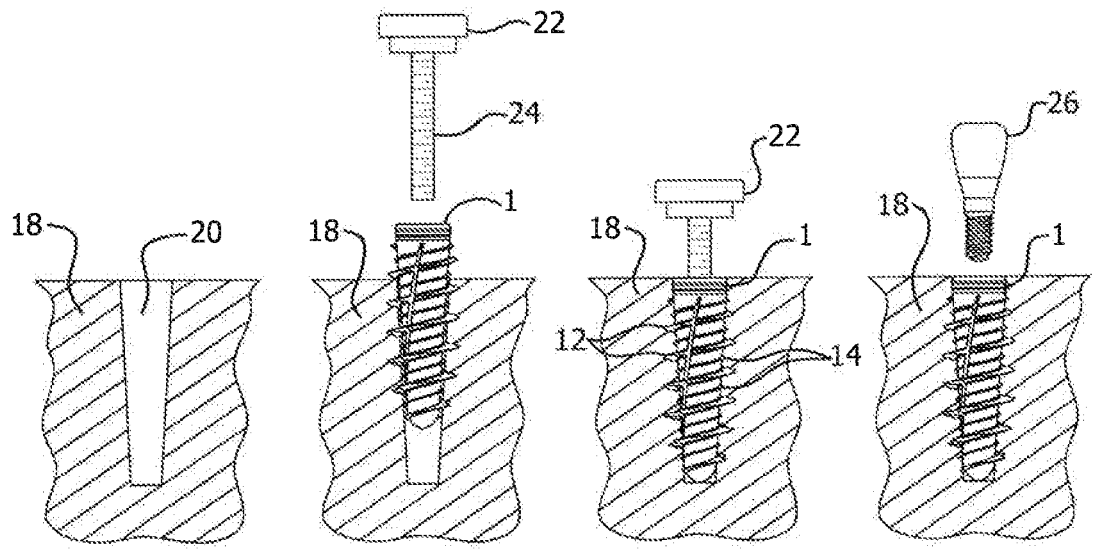
FIGS. 9-16 depicts one method of installation of the dental implant and crown according to the present invention.

Dental implant plant 1 is used as follows to install a permanent implant/dental crown unit into either the maxilla or mandible bone 18 of a patient. A small hole 20 is bored or drilled into the bone of the patient. See FIG. 9. Dental implant 1 is inserted into hole 20. A standard dental tool 22, having threads 24 which are configured to engage internal threads 10 of dental implant 1, is threadably mated with the internal threads and is then rotated in order to screw or tap dental implant 1 into hole 20 in bone 18 of the patient. See FIGS. 10 and 11. The wide pitch and deep depth of helical threads 12, with its sharp bladed edges, provide a high degree of initial stability to dental implant 1 in this process and also result in less trauma during the tapping of the dental implant into the bone. Micro-threads 14 in dental implant 1 maximizes the contact surface with the bone and provides additional support and stability during the tapping process.

In addition, as dental implant 1 is tapped down into bone 18 of the patient, loose bone material 40 is received and accumulates in channel 16. As this material travels up channel 16 as dental implant 1 is tapped down, it is expelled from the upper end of the channel. In this manner, the configuration and placement of channel 16 across helical threads 12 and 14 and its ability to expel loose cut bone material, makes the bone tapping operation go more quickly, with less impediments and, again, a less traumatic experience for the patient.

Rotation of dental tool 22 and resulting tapping of dental implant 1 continues until the top of the dental implant is substantially flush with the surface of bone 18. Dental tool 22 is then unthreaded and disengaged and removed from dental implant 1. See FIG. 11.

Figures 13, 14, 15, 16:
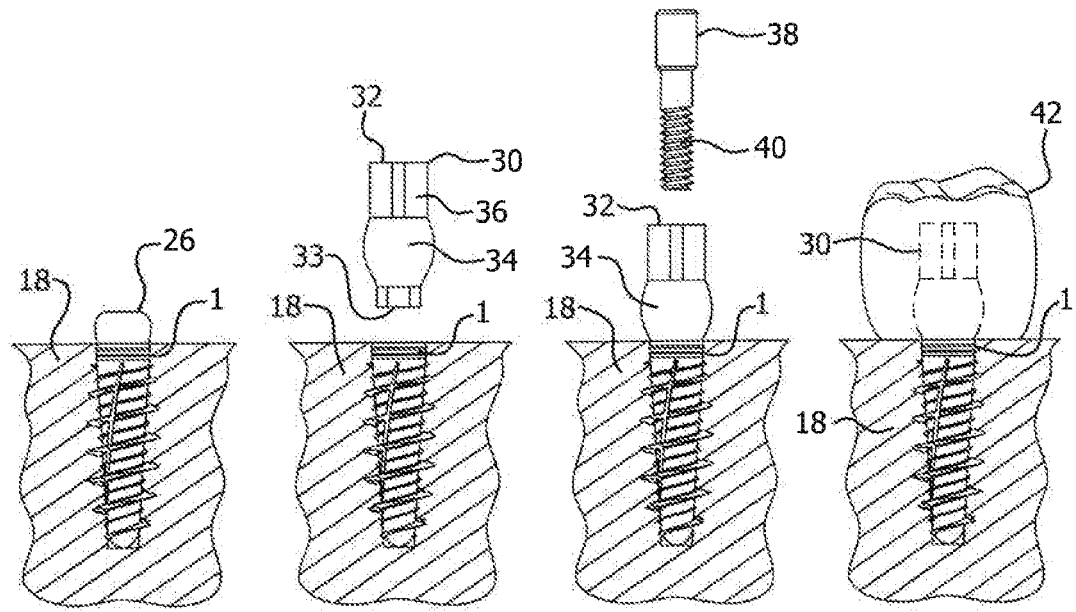
Figure 17:
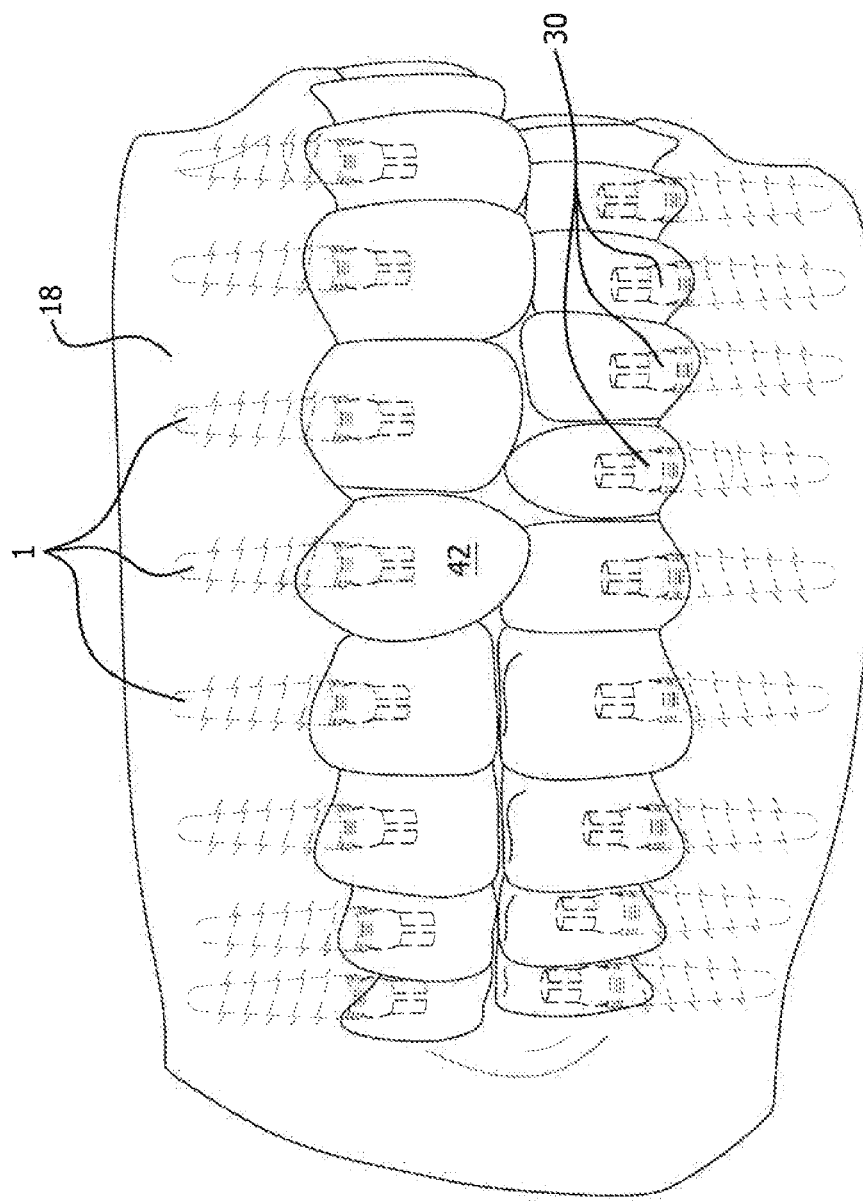
FIG. 17 is a view of a plurality of dental implants utilized to secure corresponding crowns in the mouth of a user.

Healing screw 26, having threads 28 configured to engage internal threads 10 of dental implant 1, is threadably mated with the internal threads of the dental implant. See FIG. 12. Healing screw 26 is then rotated, engaging threads 28 and internal threads 10, resulting in the healing screw being inserted into cavity 6 of dental implant 1, until the healing screw is located just above the surface of bone 18 of the patient. See FIG. 13. In this location above the bone surface, the presence of healing screw 26 provides the patient with little, if any, significant impediment in his or her eating, speaking, etc.

Given the relatively minor trauma resulting from the insertion of the dental implant 1 and healing screw into bone 18 of the patient, a period of only approximately thirty (30) days is necessary for the gum and bone healing process. At that time, healing screw 26 is unscrewed so that the threads of the healing screw and the dental implant are disengaged. Healing screw 26 is then removed from dental implant 1.

Abatement member 30 has open top 32 and bottom 33 and is substantially hollow. It has bulbous mid-section 34 and platform support section 36. Bulbous mid-section 34 of abatement member 30 is configured to contact and be positioned within and on smooth sidewalls 8 at the upper end of cavity 6. See FIG. 15. This gives abatement member 30 a high degree of stability when it is connected to implant 1.

Attachment screw 38 comprises threaded section 40. See FIG. 15. After abatement member 30 is positioned within and on sidewalls 8 of implant 1, attachment screw 38 is lowered into open top 32 of and inserted through abatement member 30, such that at least threaded section 40 of the attachment extends out of open bottom 33 of the abatement member. Threaded section 40 of attachment screw 38 is then threadedly engaged with threads 10 within cavity 6 of implant 1, in order to lock abatement member 30 to the implant.

Crown 42 is positioned over abatement member 30 and permanently attached, such that the crown rests comfortably on the gum of the patient. See FIG. 16. The curved design of mid-section 34 and configuration of platform section 36 provide excellent support for the soft tissue and gum of the patient and prevents any shoulder contact with crown 42 mounted and secured onto abatement member 30.

An alternate dental implantation method is disclosed with reference to FIGS. 18a-h to 27a-b. Conical drill 100, FIGS. 26a-c, has non-functional tip 102 which is sized at 1.5 mm. Four conical sharp blades 104 are used to bore the hole for implant 1. A slow speed is preferred and the drill can be operated manually, by the hand. The four blades are used for sharp cuts and the relatively slow rotation results in far less patient trauma. In addition, the bone does not expand very much and therefore less bone is lost. The bored hole will make tapping implant 1 fairly easy, fitting slowly into the hole to prevent heating and trauma.

Insertion of implant 1 will continue expanding the bone hole, if necessary, due to the conical shape of the implant and its helical threads 12 and 14, and channel sharp edge blade 43. Thread 12 provides high initial stability and micro-thread 14 maximizes the surface contact with the bone. Ground loose bone is removed through channel 16, surrounding implant 1. Channel 16 also provides high stability and anti-rotation forces for implant 1.

Implant 1 is thus tapped into the hole initially bored by drill 100, and fitted therein such that cylindrical, polished, external side walls 19 at the top of the implant are over the bone level.

Abatement member 48, shown in FIGS. 20a-g, has an external, pentagon shaped top section 56 which extends down until it turns into bulbous section 60. Rounded, polished edge 52, located at the bottom of section 60, has conical, 45° interior surface 58 opening into internal, hexagonal shaped cavity 50 in section 60. Cylindrical cavity 49 extends from the open top of abatement member 48, to step 54 having a rounded edge. Opening 62 connects open top 49 with hexagon cavity 50.

Sleeve 66, shown in FIGS. 21a-g, can be made of a flexible, resilient plastic or equivalent material. Flexible sleeve 66 has through channel 68. Its top section 78 is hexagonal in shape and extends down to spacer member 72 having 45° top conical surface 73 and 45° bottom conical surface 80. Bottom section 70, also hexagonal in shape, is located below spacer member 72.

Vertical slots 76 and 77 are located on opposite sides of top section 78. The slots extend through spacer member 72 and part way into bottom section 70. Vertical slots 74 and 75 are located on opposite sides of bottom section 70. The slots extend through spacer member 72 and part way into top section 78. Slots 74-77 provide the flexibility to sleeve 66, allowing micro-movement defined herein as being approximately 0.1 mm to 1.5 mm.

Dental screw 82, shown in FIGS. 22a-f, comprises head 84 with cavity 86 and threads 88. Dental screw 82 terminates at bottom end 90.

Healing screw 106, shown in FIGS. 27a-b, comprises bulbous shaped head 108 with open slot 114, tapered intermediate section 110, and lower threaded section 112. The bulbous shaped head 108 of healing screw 106 makes its use universal, since it covers the variety of different size of screws which may be needed. This makes it easier for the dentist to choose the appropriate healing screw for the thickness of the gum, and the neck size of the implant.

As previously described with regard to the method outlined and disclosed in FIGS. 9-16, a tapered hole is first bored into the bone by use of drill 100. Implant 1 is screwed into the hole, its helical threads 12 and 14 and edge blade 43 of channel 16 continuing to cut through bone, which is compelled and evacuated through the channel. Implant 1 is positioned such that its polished side walls 19 remain above the bone surface. Healing screw 106 is then threadably screwed into and engaged with threads 10 of the implant. And as previously discussed, once the first stage healing process is completed, i.e. after approximately thirty (30) days, healing screw 106 is disengaged from implant threads 10 and removed.

As best seen in FIGS. 19a-c and 23a-c, flexible sleeve 66 is inserted into cavity 6 and its hexagonal side walls 21 of implant 1, the hexagonal configuration of bottom section 70 of the sleeve mating with the hexagonal shaped side walls of the cavity. Spacer member 72 ultimately contacts conical side walls 8 of implant 1 perfectly, such that bottom section 70 of sleeve 66 remains in cavity 21 and top section 78 of the sleeve extends out of the implant.

Abatement member 48 is then positioned over sleeve 66 and compelled down until round edge 52 slightly contacts polished sidewalls 19 of implant 1 and conical interior surface 58 of the abatement member is positioned on top conical surface 73 of spacer member 72. In this position, hexagonally shaped top section 78 of sleeve 66 fits snugly into hexagonally shaped cavity 50 of abatement member 48.

Dental screw 82 is inserted into cylindrical cavity 49 of abatement member 48 and through sleeve 66 until it reaches implant 1, where its threads 88 are engaged with threads 10 of the implant. Screwing of dental screw 82 will stop when head 84 of the screw contacts rounded edge of step 54. See FIGS. 23a-c.

As seen in FIGS. 23b-c, when there are no occlusal forces impacting implant 1, round edge 52 of abatement member 48 contacts polished sidewalls 19 of the implant, thereby creating space 120. This allows abatement member 48 to move slightly up and down, dictated and controlled by the conical 45° surfaces of interior surface 58 of the abatement member, of spacer member 72 of sleeve 66, and of conical sidewalls 8, and the contact of head 84 of dental screw 84 with the rounded edge of step 54 of the abatement member. All rounded surface contacts between components allow for minute sliding movement, to keep all components balanced.

The impact of vertical occlusal forces on a properly positioned implant is illustrated in FIGS. 24a-e. Such downward forces will compel abatement member 48 down, such that its rounded edge 52 partially overlays space 120. This also transmits a horizontal force, causing top section 78 of flexible sleeve 66 to move towards and bottom section 70 to move away from screw 82. See FIG. 24c. Upward forces will compel abatement member 48 up, such that its rounded edge 52 partially overlays space 120. This also transmits a horizontal force, causing top section 78 of flexible sleeve 66 to move away from and bottom section 70 to move toward screw 82. See FIG. 24d. Slots 74-77 provide the additional flexibility to flexible sleeve 66. This allows abatement member 48 to experience micro-movement, i.e. to move only approximately 0.1 mm-0.15 mm, thereby tightly holding screw 82 at contact points 122 and 124, cushioning implant 1 as a natural tooth is cushioned, and maintaining all components in a balanced and stable position.

The configuration of slots 74-77 on sleeve 66 also allows the sleeve to accept composite forces, and, along with the contacts provided by rounded edge surfaces 52 and 54 and the rounded edge of screw head 84, to accommodate slight implant tipping movement as well. FIGS. 25a-e illustrate this action, a micro-movement of 0.1 mm-0.15 mm, which again serves to simulate the cushioning effect inherent in a natural tooth.

Certain novel features and components of this invention are disclosed in detail in order to make the invention clear in at least one form thereof. However, it is to be clearly understood that the invention as disclosed is not necessarily limited to the exact form and details as disclosed, since it is apparent that various modifications and changes may be made without departing from the spirit of the invention.

The invention claimed is:

1. A dental implant comprising a unitary body having an exterior surface and a given length extending from an open top to a bottom tip end, said body being tapered from its open top where it is widest, to its bottom tip end, the body further comprising:

smooth, cylindrical external sidewalls comprising a ring tapered from and surrounding the open top of the body;

an internal cavity extending from the open top for the majority of the length of the body, the cavity having an upper end with smooth inner conical sidewalls which taper into a lower section of the cavity, the cavity comprising internal threads extending from the inner sidewalls down into the cavity;

first helical, wide pitch threads having sharp, blade edges, said threads being located along the exterior surface of the body and extending the length of the body from the open top to the bottom tip end;

second helical, micro-threads having sharp, blade edges, said threads being located along and extending out from the exterior surface of the body, only one of the second threads being located between two contiguous first threads; and a channel encircling the exterior surface of the body no more than one time and running in a single oblique path directly from a location below the open top to a location above the bottom tip end, said channel extending through all of the first and second threads and comprising a sharp, bone cutting edge blade.

* * * * *